(12) United States Patent
Meyering et al.

(10) Patent No.: US 8,871,819 B2
(45) Date of Patent: Oct. 28, 2014

(54) GLYCEROL ESTER ACTIVE AGENT DELIVERY SYSTEMS AND METHODS

(75) Inventors: Emily R. R. Meyering, Eden Praire, MN (US); Stephen J. Chudzik, St. Paul, MN (US)

(73) Assignee: SurModics, Inc., Eden Prairie, MN (US)

( * ) Notice: Subject to any disclaimer, the term of this patent is extended or adjusted under 35 U.S.C. 154(b) by 197 days.

(21) Appl. No.: 13/104,383

(22) Filed: May 10, 2011

(65) Prior Publication Data

US 2011/0275725 A1 Nov. 10, 2011

Related U.S. Application Data

(60) Provisional application No. 61/333,036, filed on May 10, 2010.

(51) Int. Cl.
| | | |
|---|---|---|
| *A01N 25/00* | (2006.01) | |
| *A61L 31/16* | (2006.01) | |
| *A61L 27/34* | (2006.01) | |
| *A61L 27/54* | (2006.01) | |
| *A61L 29/08* | (2006.01) | |
| *A61L 29/16* | (2006.01) | |
| *A61L 31/10* | (2006.01) | |

(52) U.S. Cl.
CPC ............... *A61L 31/16* (2013.01); *A61L 27/34* (2013.01); *A61L 27/54* (2013.01); *A61L 29/085* (2013.01); *A61L 29/16* (2013.01); *A61L 31/10* (2013.01); *A61L 2300/00* (2013.01)
USPC ............................. 514/786; 514/772; 525/450

(58) Field of Classification Search
CPC combination set(s) only.
See application file for complete search history.

(56) References Cited

U.S. PATENT DOCUMENTS

| | | | |
|---|---|---|---|
| 3,936,391 A | | 2/1976 | Gabby et al. |
| 4,456,627 A | | 6/1984 | Van Heteren et al. |
| 4,490,421 A | | 12/1984 | Levy |
| 5,002,582 A | * | 3/1991 | Guire et al. ............ 427/2.24 |
| 5,073,641 A | * | 12/1991 | Bundgaard et al. ......... 560/56 |
| 5,466,719 A | | 11/1995 | Jakobson et al. |
| 5,502,219 A | | 3/1996 | Harris |
| 5,556,383 A | | 9/1996 | Wang et al. |
| 5,585,506 A | | 12/1996 | Harvey et al. |
| 5,728,732 A | | 3/1998 | Corey et al. |
| 5,891,451 A | | 4/1999 | Guerrero et al. |
| 6,168,748 B1 | | 1/2001 | Wang et al. |
| 6,210,364 B1 | | 4/2001 | Anderson et al. |
| 6,328,710 B1 | | 12/2001 | Wang et al. |
| 6,482,348 B1 | | 11/2002 | Wang et al. |
| 6,620,904 B2 | | 9/2003 | Lemke |
| 2005/0255142 A1 | * | 11/2005 | Chudzik et al. ............ 424/426 |
| 2006/0240194 A1 | | 10/2006 | Lemke |
| 2007/0065481 A1 | | 3/2007 | Chudzik |
| 2007/0154591 A1 | | 7/2007 | Andersen |
| 2007/0155906 A1 | | 7/2007 | Hissink et al. |
| 2007/0218102 A1 | | 9/2007 | Chudzik et al. |
| 2007/0224247 A1 | | 9/2007 | Chudzik et al. |
| 2007/0260054 A1 | | 11/2007 | Chudzik |
| 2010/0015240 A1 | | 1/2010 | Biggs |

FOREIGN PATENT DOCUMENTS

| | | |
|---|---|---|
| EP | 1430917 | 6/2004 |
| EP | 1994950 | 11/2008 |
| WO | WO-2009051614 | 4/2009 |
| WO | WO-2011143237 | 11/2011 |

OTHER PUBLICATIONS

Dow Corning, a guide to Silane Solutions, 2005.*
Orafei, Hossein et al., "Novel Poly(glycerol-adipate) Polymers Used for Nanoparticle Making: A Study of Surface Free Energy", Iranian Journal of Pharmaceutical Research (2008), 7 (1): 11-19 2008, pp. 11-19.
Santoyo, Antonio B. et al., "Biosynthesis of Polyglycerol Polyricinoleate (PGPR) with *Rhizopus Arrhizus* Lipase", Journal of Biotechnology 131S (2007) S74-S94 2007, S82.
Howes, D et al., "The Fate of Ingested Glyceran Esters of Condensed Castor Oil Fatty Acids [Polyglycerol Polyricinoleate (PGPR)] in the Rat", Food and Chemical Toxicology 36, pp. 719-773, 1998.
Charlemagne, D et al., "Enzymatic Synthesis of Polyglycerol-Fatty Acid Esters in a Solvent-Free System", Journal for American Oil Chemists' Society vol. 72. No. 1 (1995), pp. 61-65.
Akiyama, Yohko et al., "In Vitro and in Vivo evaluation of Mucoadhesive Microspheres Prepared for the Gastrointestinal Tract Using Polyglycerol Esters of Fatty Acids and a Poly(acrylic acid) Derivative", Pharmaceutical Research, vol. 12, No. 3, 1995, pp. 397-405.
FAO Nutrition Meetings Report, "Toxicological Evaluation of Some Antimicrobials, Antioxidants, Emulsifiers, Stabilizers, Flour-treatment Agents, Acids and Bases", FAO Nutrition Meetings Report Series No. 40A, B, C WHO/ Food Add. 67.29 1966, pp. 1-4.
Dobson, Kevin S. et al., "The Preparation of Polyglycerol Esters Suitable as Low-Caloric Fat Substitutes", Journal of the American Oil Chemists' Society vol. 70, No. 11 (Nov. 1993), 1089-1092.

(Continued)

*Primary Examiner* — Wu-Cheng Winston Shen
*Assistant Examiner* — Jean Cornet
(74) *Attorney, Agent, or Firm* — Pauly, DeVries, Smith & Deffner, LLC

(57) ABSTRACT

Embodiments of the invention include glycerol esters and use of the same for active agent delivery systems and methods. In an embodiment, the invention includes an active agent eluting device including a glycerol ester, an active agent dispersed within the glycerol ester, the active agent eluting device configured to elute the active agent from the glycerol ester in response to degradation of the glycerol ester. In an embodiment, the invention includes a composition including a glycerol ester; an active agent dispersed within the glycerol ester; the active agent eluting device configured to elute the active agent from the glycerol ester in response to degradation of the glycerol ester. Other embodiments are also included herein.

18 Claims, 2 Drawing Sheets

(56) References Cited

OTHER PUBLICATIONS

McIndtyre, R T., "Polyglycerol esters", Journal of American Oil Chemists' Society Nov. 1979 (vol. 56), pp. 835A-840A.

Puri, Sanyogita, "Drug Incorporation and Release of Water Soluble Drugs from Novel Functionalized Poly(glycerol adipate) Nanoparticles", Journal of Controlled Release 125 (2005), Oct. 10, 2007, pp. 59-67.

Bodansky, M et al., "Utilization of Polyglycerol Esters", Biochemistry vol. 32 Aug. 30, 1938, pp. 1938-1942.

Solvay Chemicals, , "Polyglycerols for Ester Production", PGLC-05-002 Revised Aug. 2008 CGR4004, From www.solvaychemicals.us Aug. 2008, pp. 1-7.

Takatori, Toshihito, "Design of Controlled-Release Morphine Suppositories Containing Polyglycerol Ester Acid", Biologicaal Pharmacy Bulletin 28(8) 1480-1484 (2005), vol. 8, pp. 1480-1484.

Babayan, V K., "Preparation and Properties of Some Polyglycerol Esters of Short and Medium Length Fatty Acids", Journal of the American Oil Chemists' Society Jul. 1971, pp. 307-309.

Babayan, V K. et al., "Nutritional Studies of Polyglycerol Esters", The Journal of the American Oil Chemist' Society vol. 41, Jun. 1964, pp. 434-438.

Hegemeier, C J., "Ocular Tolerability of Poly(lactide-co-glyoliide) Microspheres Following Subconjunctival and Inravitreal Injection in Rabbit Eyes", ARVO 2010 Presented ARVO 2010, Hall B/C, May 6, 2010.

Kallinteri, Paraskevi et al., "Novel Functionalized Biodegradable Polymers for Nanoparticle Drug Delivery Systems", Biomacromolecules 2005 American Chemical Society, pp. 1885-1894.

Yamagata, Yutaka et al., "Novel Sustained Release Dosage Forms of Proteins Using Polyglycerol Esters of Fatty Acids", Journal of Controlled Release vol. 63, Issue 3 Feb. 3, 2003, 319-329.

De Meulenaer, B et al., "Development of Chromatographic Method for the Determination of Degree of Polymerisation of Polyglycerols and Polyglycerol Fatty Acid Esters", Chromatographia vol. 51, No. 1/2, Jan. 2000, 44-52.

PCT International Search Report and Written Opinion from International Application No. PCT/US2011/035951, mailed Aug. 3, 2011, pp. 1-12, 2 Pgs.

* cited by examiner

GLYCEROL ESTER ACTIVE AGENT DELIVERY SYSTEMS AND METHODS

This application claims the benefit of U.S. Provisional Application No. 61/333,036, filed May 10, 2010, the contents of which are herein incorporated by reference.

FIELD OF THE INVENTION

The present invention relates to compositions and use of the same for active agent delivery systems and methods. More specifically, the present invention relates to glycerol esters and use of the same for active agent delivery systems and methods.

BACKGROUND OF THE INVENTION

Therapeutic benefits can be achieved in some instances by providing an active agent to a specific, localized target tissue, instead of systemically. In this manner, the effect of the agent on the target tissue can be maximized while limiting side effects on other tissues. Therapeutic benefits can also be achieved by providing an active agent to a subject in a manner that provides controlled release of the active agent.

One approach to providing these benefits is to use a matrix which retains an active agent before releasing through processes such as diffusion. Another approach to providing these benefits is to use a degradable matrix which retains an active agent before releasing it as the degradable matrix breaks down. Degradable matrices offer the advantage of being able to control the release rate of active agents that do not readily diffuse through non-degradable coatings. In some case, degradable components can be combined with non-degradable components to form hybrid degradable/non-degradable active agent release matrices.

A lipase is a water-soluble enzyme that catalyzes the hydrolysis of ester bonds in water-insoluble, lipid substrates. Lipases comprise a subclass of the esterases. Lipases perform important roles in the digestion, transport and processing of dietary lipids and are thus present in most living organisms. For example, human pancreatic lipase, which is the main enzyme to break down fats in the human digestive system, converts triglyceride substrates found in ingested oils to monoglycerides and free fatty acids.

SUMMARY OF THE INVENTION

Embodiments of the invention include glycerol esters and use of the same for active agent delivery systems and methods. In an embodiment, the invention includes an active agent eluting device including a glycerol ester, an active agent dispersed within the glycerol ester, the active agent eluting device configured to elute the active agent from the glycerol ester.

In an embodiment, the invention includes a medical device including a block copolymer of the formulae AB, ABA, BAB, or mixtures thereof wherein A represents a glycerol ester block and B represents at least one block selected from the group consisting of poly-lactide-co-glycolide (PLGA) and polyethylene glycol (PEG), polyesters, polyurethanes, and polycarbonates wherein the B block comprises about 1 to about 99 wt. % of the copolymer.

In an embodiment, the invention includes a composition including a glycerol ester; an active agent dispersed within the glycerol ester; the active agent eluting device configured to elute the active agent from the glycerol ester.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE FIGURES

The invention may be more completely understood in connection with the following drawings, in which.

Figure 1:
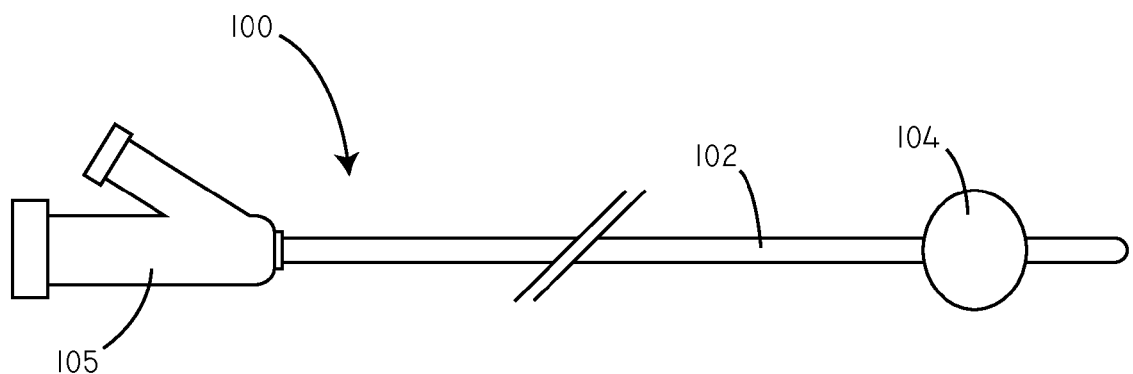
FIG. 1 is a schematic view of a device in accordance with an embodiment herein.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Embodiments herein include compounds, such as glycerol esters and glycerol ester polymers, and active agent delivery devices and systems including the same. The ester bonds in the glycerol esters can be subject to degradation with lipases, rendering the glycerol ester degradable under physiologic conditions. In an embodiment, the invention can include an active agent eluting device or composition including a glycerol ester; an active agent dispersed within the glycerol ester; the active agent eluting device configured to elute the active agent from the glycerol ester in response to degradation of the glycerol ester.

It will be appreciated that glycerol esters in accordance with embodiments herein can be formed in various ways. By way of example, a glycerol can be reacted with a carboxylic acid in order to form a glycerol ester. As another example, a glycerol can be reacted with an acid chloride to form a glycerol ester. Other techniques are also possible. Exemplary glycerols can include glycerol, glycerol oligomers, and glycerol polymers. Structure (I) below is an example of a glycerol polymer. In various embodiments, n can be from 1 to about 1500.

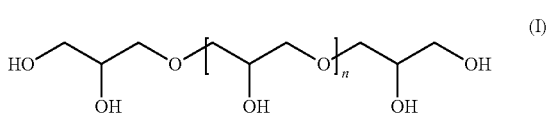

(I)

Specific glycerols can include glycerol, tetraglycerol, hexaglycerol, decaglycerol, and the like. Carboxylic acids can with lipid numbers C2 to C24. Carboxylic acids can include those that are fully saturated, monounsaturated, polyunsaturated, and the like, including but not limited to lipid numbers C2:0 to C24:12. Exemplary carboxylic acids can specifically include hexanoic acid, octanoic acid, and decanoic acid. Exemplary carboxylic acids can also include essential fatty acids including, but not limited to, omega-3 and omega-6. Well not intending to be bound by theory, the use of essential fatty acids can be advantageous because as the glycerol ester is broken down in vivo it can provide essential fatty acids to the patient. Various fatty acids can be selected based on desired physical properties of the resulting glycerol ester. By way of example, some fatty acids can promote formation of crystalline material, some fatty acids can promote formation of a wax-like material, still others can promote formation of a liquid material.

Exemplary acid chlorides can include having carbon chains similar to those for carboxylic acids. Exemplary acid chlorides can specifically include hexanoyl chloride, octanoyl chloride, decanoyl chloride, and the like.

Embodiments herein can also include glycerol ester polymers. For example, embodiments herein can include glycerol ester polymers wherein the glycerol esters form a polymeric backbone. Structure (II) is an example of a glycerol ester polymer. In various embodiments, n can be from 1 to about 1500. $X_1$ and $X_2$ can be any of various functional groups including, but not limited to, hydroxyl groups, blocks forming a block copolymer as described below, fatty acid ester groups, or the like.

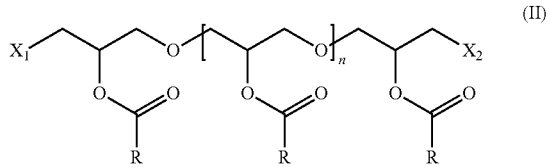

(II)

Glycerol ester polymers can be formed through various techniques. An approach to synthesis of an esterified product suitable for free-radical polymerization is illustrated below in Example 22. Similarly, an approach to synthesis of an esterified product suitable for nucleophilic reaction with a hydrazide-reactive group is illustrated below in Example 23. However, it will be appreciated that other approaches can also be used. Such materials can then be polymerized through standard techniques including chain polymerization, condensative chain polymerization, polycondensation, and polyaddition. In some cases simple glycerol or polyglycerol starting materials can be directly (e.g., without prior end modification) polymerized to form polyglycerol polymers with greater than 10 glycerol subunits.

While not intending to be bound by theory, it is believed that increasing the molecular weight from glycerol oligomers to glycerol polymers can be beneficial for many reasons. For example, when configured as an injectable depot delivery system, it is desirable to have the material stay together in form in the body. Increasing the molecular weight of the polymer will increase the chain entanglement, which increases the strength of the materials and makes them more prone to remain in a particular shape. Additionally, the summation of intermolecular forces is greater as one increases the molecular weight of a polymer. Increasing these help the polymers stick together and bind the chains together. Glycerol ester polymers in accordance with embodiments herein can have molecular weights above 5,000. In some embodiments glycerol ester polymer in accordance with embodiments herein can have molecular weight above 10,000.

In some embodiments, glycerol esters can be extended off the backbone of other degradable biocompatible polymers. For example, glycerol esters can be attached to naturally occurring polymers such as peptides, proteins, polysaccharides to provide a mechanical property or attach active agents. Glycerol esters can also be attached to polyhydroxy or polyamine compounds such as poly(vinyl alcohol), polyesters and polyamides. In some embodiments it can be advantageous to couple glycerol esters to other polymeric backbones to help solubilize an active ingredient or change the physical polymer properties to make them more fitting for a particular application.

In some embodiments, the glycerol backbone can be fully esterified. In other embodiments, the glycerol backbone is only partially esterified. The degree of esterification can be described with reference to the percentage of hydroxyl groups on the glycerol backbone that are esterified. As used herein, the term "fully esterified" shall refer a glycerol molecule wherein all hydroxyl groups on the backbone are esterified. The term "partially esterified" shall refer to a glycerol molecule wherein less than all of the hydroxyl groups on the backbone are esterified. In some embodiments, at least about 80% of the hydroxyl groups on the backbone are esterified. In some embodiments, at least about 90% of the hydroxyl groups on the backbone are esterified.

In some embodiments herein the glycerol ester composition can be configured to have a melting temperature ($T_m$) of greater than or equal to 25 degrees Celsius and less than or equal to 37 degrees Celsius. Such an embodiment can result in a solid at room temperature that melts at human physiological temperatures. It is believed that the melting temperature can be affected by various factors including the ester group(s) carbon chain length, backbone molecular weight, the degree of saturation of the ester group(s) carbon chain, the number of ester groups on the glycerol backbone, and the like. In some embodiments, at least one ester group can include a carbon chain with greater than or equal to two carbon atoms. In some embodiments, at least one ester group can include a carbon chain with greater than or equal to six carbon atoms. In some embodiments, at least one ester group can include a carbon chain with greater than or equal to ten carbon atoms.

In some embodiments, the melting temperature ($T_m$) point can be less than 25 degrees Celsius. Typically, solvents have low melting points so that when refrigerated or frozen, they remain flowable. Glycerol esters synthesized to be used as a biocompatible degradable solvent, for example, could benefit from a relatively low melting point. Also, it can be beneficial to store reagents and active agents at cooler temperatures to increase stability of the active agent. Additionally, a relatively low melting point provides extended flowability of the polymer and ultimately a less viscous solution at room temperature.

In some embodiments, the glycerol ester can be formed into a coating, film, or article along with an active agent and where release of the active agent is associated with the melting of the glycerol ester. By way of example, an active agent can be disposed within a glycerol ester matrix configured so that the active agent does not substantially elute out of the glycerol ester matrix when the glycerol ester matrix is in a solid form. Then, when the glycerol ester matrix reaches a melting point the active agent can release from the glycerol ester matrix as it melts. For example, the melting point could be at or near body temperature such that active agent release from the glycerol ester matrix after the glycerol ester matrix is inserted into a human subject.

In some embodiments herein the glycerol ester can include a pendant active agent or proagent as part of the ester group. As such, cleavage of the ester bond during degradation of the glycerol ester can serve to release the active agent or proagent. Inclusion of a pendant active agent or proagent can be in addition to, or in place of, a first active agent dispersed within the glycerol ester composition.

It will be appreciated that pendant active agents can include a wide variety of active agents, including, but not limited to those described in the active agents section below. In some embodiments, the active agent is an anti-inflammatory. In some embodiments, the active agent is a carboxylic acid. In an embodiment, the active agent is salicylic acid.

In some embodiments, the glycerol ester can be bonded to a substrate. By way of example, bonding the glycerol ester to a substrate can facilitate securing the glycerol ester in place. It will be appreciated that there are various ways of bonding the glycerol polymer to a substrate, depending type of substrate contemplated. By way of example, silane compounds can be used to bond glycerol esters to inorganic substrates, such as a metal. Chlorine, nitrogen, alkyloxy groups, or acetoxy groups coupling directly to silicon can produce chlorosilanes, silylamines (silazanes), alkoxysilanes, and acyloxysilanes respectively. Silane compounds of the invention can include these types of reactive silane moieties. Specifically, organofunctional alkoxysilanes can be used to couple glycerol esters to inorganic substrates. In an embodiment, the silane compound can have one or more tri(C1-C3)alkoxysilyl groups. Suitable groups include trimethoxysilyl, triethoxysilyl, and tripropoxysilyl, and combinations thereof.

The silane compound, a hydrolysis (or solvolysis) reaction product of the silane compound, a polymeric reaction product formed from the hydrolysis reaction product, or a combination thereof can bind to the surface of the inorganic substrate by reacting with oxide or hydroxide groups on the surface of the inorganic substrate. A covalent bond forms between the inorganic substrate and at least one compound in the base coating layer. The substrate can be treated to generate hydroxide or oxide groups on the surface. For example, the substrate can be treated with a strong base such as sodium hydroxide, ammonium hydroxide, and the like. In the case of a metal, the metal can be subjected to an oxidizing potential to generate oxide or hydroxide sites on the surface of the metal.

Another exemplary method of attachment can involve amide coupling. For example, the pendent hydroxyl groups on the glycerol ester can be modified to be an amine and react with carboxylic acid residues of a different substrate or material to yield a stable amide linkage. These couplings can be performed under standard conditions and do not require large amounts of heat or catalyst to proceed. In addition, urethane linkages can also be used for coupling substrates. The pendent hydroxyl group(s) on the glycerol ester can react with an isocyanate group on another substrate or material to yield a stable urethane linkage. These reactions also proceed under gentle conditions.

As another example, photoreactive groups can be used to bond a glycerol ester to a substrate in accordance with embodiments herein. The photoreactive groups can be activated leading to the formation of covalent bonds. In one approach, photoreactive groups can be introduced into glycerol esters disclosed herein, such as on the glycerol backbone or on a pendant group. Alternatively, cross-linking agents including photoreactive groups can be used to bond the glycerol ester to a substrate.

As used herein, the phrases "latent photoreactive group" and "photoreactive group" are used interchangeably and refer to a chemical moiety that is sufficiently stable to remain in an inactive state (i.e., ground state) under normal storage conditions but that can undergo a transformation from the inactive state to an activated state when subjected to an appropriate energy source. Photoreactive groups respond to specific applied external stimuli to undergo active specie generation with resultant covalent bonding to an adjacent chemical structure. For example, in an embodiment, a photoreactive group can be activated and can abstract a hydrogen atom from an alkyl group. A covalent bond can then form between the compound with the photoreactive group and the compound with the C—H bond. Suitable photoreactive groups are described in U.S. Pat. No. 5,002,582, the disclosure of which is incorporated herein by reference.

Photoreactive groups can be chosen to be responsive to various portions of actinic radiation. Typically, groups are chosen that can be photoactivated using either ultraviolet or visible radiation. Suitable photoreactive groups include, for example, azides, diazos, diazirines, ketones, and quinones. The photoreactive groups generate active species such as free radicals including, for example, nitrenes, carbenes, and excited states of ketones upon absorption of electromagnetic energy.

In some embodiments, the photoreactive group is an aryl ketone, such as acetophenone, benzophenone, anthrone, and anthrone-like heterocycles (i.e., heterocyclic analogs of anthrone such as those having N, O, or S in the 10-position), or their substituted (e.g., ring substituted) derivatives. Examples of aryl ketones include heterocyclic derivatives of anthrone, including acridone, xanthone, and thioxanthone, and their ring substituted derivatives. Other suitable photoreactive groups include quinone such as, for example anthraquinone.

The functional groups of such aryl ketones can undergo multiple activation/inactivation/reactivation cycles. For example, benzophenone is capable of photochemical excitation with the initial formation of an excited singlet state that undergoes intersystem crossing to the triplet state. The excited triplet state can insert into carbon-hydrogen bonds by abstraction of a hydrogen atom (from a polymeric coating layer, for example), thus creating a radical pair. Subsequent collapse of the radical pair leads to formation of a new carbon-carbon bond. If a reactive bond (e.g., carbon/hydrogen) is not available for bonding, the ultraviolet light-induced excitation of the benzophenone group is reversible and the molecule returns to ground state energy level upon removal of the energy source. Photoreactive aryl ketones such as benzophenone and acetophenone can undergo multiple reactivations in water and hence can provide increased coating efficiency.

The azides constitute another class of photoreactive groups and include arylazides ($C_6R_5N_3$) such as phenyl azide and 4-fluoro-3-nitrophenyl azide; acyl azides (—CO—$N_3$) such as benzoyl azide and p-methylbenzoyl azide; azido formates (—O—CO—$N_3$) such as ethyl azidoformate and phenyl azidoformate; sulfonyl azides (—$SO_2$—$N_3$) such as benzenesulfonyl azide; and phosphoryl azides $(RO)_2PON_3$ such as diphenyl phosphoryl azide and diethyl phosphoryl azide.

Diazo compounds constitute another class of photoreactive groups and include diazoalkanes (—$CHN_2$) such as diazomethane and diphenyldiazomethane; diazoketones (—CO—CHN$_2$) such as diazoacetophenone and 1-trifluoromethyl-1-diazo-2-pentanone; diazoacetates (—O—CO—CHN$_2$) such as t-butyl diazoacetate and phenyl diazoacetate; and beta-keto-alpha-diazoacetates (—CO—CN$_2$—CO—O—) such as t-butyl alpha diazoacetoacetate.

Other photoreactive groups include the diazirines (—CHN$_2$) such as 3-trifluoromethyl-3-phenyldiazirine; and ketenes (—CH=C=O) such as ketene and diphenylketene.

It will be appreciated that other chemistries beyond silanes and photoreactive groups can also be used to bond glycerol esters to substrates.

In some embodiments, glycerol esters can be used as a biocompatible solvent for other polymers. A solvent, as used herein, is an agent that dissolves a solid, liquid, or gaseous solute, resulting in a solution that is soluble in a certain volume of solvent at a specified temperature. By way of example, glycerol esters can be combined with a solute in the form of other polymers or components. The ability of an agent to serve as a solvent is dependent on its physical properties such as polarity manifested as hydrophobicity and hydrophilicity. In this regard, the glycerol ester can be manipulated through selection and/or modification of the ester group carbon chains, the number of ester groups on the glycerol backbone, and/or the addition of pendant groups having specific physical properties, in order to have the proper physical properties to serve as a solvent for a given component.

Exemplary solutes can include various polymers, including but not limited to degradable polymers. As one example, degradable polymers of the invention can include multi-block copolymers, comprising at least two hydrolysable segments derived from pre-polymers A and B, which segments are linked by a multi-functional chain-extender and are chosen from the pre-polymers A and B, and triblock copolymers ABA and BAB, wherein the multi-block copolymer is amorphous and has one or more glass transition temperatures (Tg) of at most 37° C. (Tg) at physiological (body) conditions. The pre-polymers A and B can be a hydrolysable polyester, polyetherester, polycarbonate, polyestercarbonate, polyanhydride or copolymers thereof, derived from cyclic monomers such as lactide (L,D or L/D), glycolide, ε-caprolactone, δ-valerolactone, trimethylene carbonate, tetramethylene carbonate, 1,5-dioxepane-2-one, 1,4-dioxane-2-one (para-dioxanone) or cyclic anhydrides (oxepane-2,7-dione). The composition of the pre-polymers may be chosen in such a way that the maximum glass transition temperature of the resulting copolymer is below 37° C. at body conditions. To fulfill the requirement of a Tg below 37° C., some of the above-mentioned monomers or combinations of monomers may be more preferred than others. This may by itself lower the Tg, or the pre-polymer is modified with a polyethylene glycol with sufficient molecular weight to lower the glass transition temperature of the copolymer. The degradable multi-block copolymers can include hydrolysable sequences being amorphous and the segments may be linked by a multifunctional chain-extender, the segments having different physical and degradation characteristics. For example, a multi-block co-polyester including a glycolide-ε-caprolactone segment and a lactide-glycolide segment can be composed of two different polyester pre-polymers. By controlling the segment monomer composition, segment ratio and length, a variety of polymers with properties that can easily be tuned can be obtained. Such degradable multi-block copolymers can specifically include those described in U.S. Publ. App. No. 2007/0155906, the content of which is herein incorporated by reference in its entirety.

Degradable polymers can also include polysaccharides and modified polysaccharides such as starch, cellulose, chitin, chitosan, and copolymers thereof. Hydrophobic derivatives of natural degradable polysaccharide refer to a natural degradable polysaccharide having one or more hydrophobic pendent groups attached to the polysaccharide. In many cases the hydrophobic derivative includes a plurality of groups that include hydrocarbon segments attached to the polysaccharide. When a plurality of groups including hydrocarbon segments are attached, they are collectively referred to as the "hydrophobic portion" of the hydrophobic derivative. The hydrophobic derivatives therefore include a hydrophobic portion and a polysaccharide portion.

The polysaccharide portion can include a natural degradable polysaccharide, which refers to a non-synthetic polysaccharide that is capable of being enzymatically degraded. Natural degradable polysaccharides include polysaccharide and/or polysaccharide derivatives that are obtained from natural sources, such as plants or animals. Natural degradable polysaccharides include any polysaccharide that has been processed or modified from a natural degradable polysaccharide (for example, maltodextrin is a natural degradable polysaccharide that is processed from starch). Exemplary natural degradable polysaccharides include maltodextrin, amylose, cyclodextrin, polyalditol, hyaluronic acid, dextran, heparin, chondroitin sulfate, dermatan sulfate, heparan sulfate, keratan sulfate, dextran, dextran sulfate, pentosan polysulfate, and chitosan. Specific polysaccharides are low molecular weight polymers that have little or no branching, such as those that are derived from and/or found in starch preparations, for example, maltodextrin, amylose, and cyclodextrin. Therefore, the natural degradable polysaccharide can be a substantially non-branched or completely non-branched poly(glucopyranose) polymer.

Another contemplated class of natural degradable polysaccharides is natural degradable non-reducing polysaccharides. A non-reducing polysaccharide can provide an inert matrix thereby improving the stability of active pharmaceutical ingredients (APIs), such as proteins and enzymes. A non-reducing polysaccharide refers to a polymer of non-reducing disaccharides (two monosaccharides linked through their anomeric centers) such as trehalose (α-D-glucopyranosyl α-D-glucopyranoside) and sucrose (β-D-fructofuranosyl α-D-glucopyranoside). An exemplary non-reducing polysaccharide includes polyalditol which is available from GPC (Muscatine, Iowa). In another aspect, the polysaccharide is a glucopyranosyl polymer, such as a polymer that includes repeating (1→3)O-β-D-glucopyranosyl units.

Dextran is an α-D-1,6-glucose-linked glucan with side-chains 1-3 linked to the backbone units of the dextran biopolymer. Dextran includes hydroxyl groups at the 2, 3, and 4 positions on the glucopyranose monomeric units. Dextran can be obtained from fermentation of sucrose-containing media by *Leuconostoc mesenteroides* B512F.

Dextran can be obtained in low molecular weight preparations. Enzymes (dextranases) from molds such as *Penicillium* and *Verticillium* have been shown to degrade dextran. Similarly many bacteria produce extracellular dextranases that split dextran into low molecular weight sugars.

Chondroitin sulfate includes the repeating disaccharide units of D-galactosamine and D-glucuronic acid, and typically contains between 15 to 150 of these repeating units. Chondroitinase AC cleaves chondroitin sulfates A and C, and chondroitin.

Hyaluronic acid (HA) is a naturally derived linear polymer that includes alternating β-1,4-glucuronic acid and β-1,3-N-acetyl-D-glucosamine units. HA is the principal glycosaminoglycan in connective tissue fluids. HA can be fragmented in the presence of hyaluronidase.

In many aspects the polysaccharide portion and the hydrophobic portion include the predominant portion of the hydrophobic derivative of the natural degradable polysaccharide. Based on a weight percentage, the polysaccharide portion can be about 25% wt of the hydrophobic derivative or greater, in the range of about 25% to about 75%, in the range of about 30% to about 70%, in the range of about 35% to about 65%, in the range of about 40% to about 60%, or in the range of about 45% to about 55%. Likewise, based on a weight percentage of the overall hydrophobic derivative, the hydrophobic portion can be about 25% wt of the hydrophobic derivative or greater, in the range of about 25% to about 75%, in the range of about 30% to about 70%, in the range of about 35% to about 65%, in the range of about 40% to about 60%, or in the range of about 45% to about 55%. In exemplary aspects, the hydrophobic derivative has approximately 50% of its weight attributable to the polysaccharide portion, and approximately 50% of its weight attributable to its hydrophobic portion.

The hydrophobic derivative has the properties of being insoluble in water. The term for insolubility is a standard term used in the art, and meaning 1 part solute per 10,000 parts or greater solvent. (see, for example, Remington: The Science and Practice of Pharmacy, 20th ed. (2000), Lippincott Williams & Wilkins, Baltimore Md.).

A hydrophobic derivative can be prepared by associating one or more hydrophobic compound(s) with a natural degradable polysaccharide polymer. Methods for preparing hydrophobic derivatives of natural degradable polysaccharides are described herein.

In some embodiments, a "pendant group" can refer to a group of covalently bonded carbon atoms having the formula $(CH_n)_m$, wherein m is 2 or greater, and n is independently 2 or 1. A hydrocarbon segment can include saturated hydrocarbon groups or unsaturated hydrocarbon groups, and examples thereof include alkyl, alkenyl, alkynyl, cyclic alkyl, cyclic alkenyl, aromatic hydrocarbon and aralkyl groups. Specifically, the pendant group includes linear, straight chain or branched $C_1$-$C_{20}$ alkyl group; an amine terminated hydrocarbon or a hydroxyl terminated hydrocarbon. In another embodiment, the pendant group includes polyesters such as polylactides, polyglycolides, poly(lactide-co-glycolide) copolymers, polycaprolactone, terpolymers of poly(lactide-co-glycolide-co-caprolatone), or combinations thereof.

Various factors can be taken into consideration in the synthesis of the hydrophobic derivative of the natural degradable polysaccharide. These factors include the physical and chemical properties of the natural degradable polysaccharide, including its size, and the number and presence of reactive groups on the polysaccharide and solubility, the physical and chemical properties of the compound that includes the hydrocarbon segment, including its the size and solubility, and the reactivity of the compound with the polysaccharide.

In preparing the hydrophobic derivative of the natural degradable polysaccharide any suitable synthesis procedure can be performed. Synthesis can be carried out to provide a desired number of groups with hydrocarbon segments pendent from the polysaccharide backbone. The number and/or density of the pendent groups can be controlled, for example, by controlling the relative concentration of the compound that includes the hydrocarbon segment to the available reactive groups (e.g., hydroxyl groups) on the polysaccharide.

The type and amount of groups having the hydrocarbon segment pendent from the polysaccharide is sufficient for the hydrophobic polysaccharide to be insoluble in water. In order to achieve this, as a general approach, a hydrophobic polysaccharide is obtained or prepared wherein the groups having the hydrocarbon segment pendent from the polysaccharide backbone in an amount in the range of 0.25 (pendent group): 1 (polysaccharide monomer) by weight.

The weight ratio of glucopyranose units to pendent groups can vary, but will typically be about 1:1 to about 100:1. Specifically, the weight ratio of glucopyranose units to pendent groups can be about 1:1 to about 75:1, or about 1:1 to about 50:1. Additionally, the nature and amount of the pendent group can provide a suitable degree of substitution to the polysaccharide. Typically, the degree of substitution will be in the range of about 0.1-5 or about 0.5-2.

To exemplify these levels of derivation, very low molecular weight (less than 10,000 Da) glucopyranose polymers are reacted with compounds having the hydrocarbon segment to provide low molecular weight hydrophobic glucopyranose polymers. In one mode of practice, the natural degradable polysaccharide maltodextrin in an amount of 10 g (MW 3000-5000 Da; ~3 mmols) is dissolved in a suitable solvent, such as tetrahydrofuran. Next, a solution having butyric anhydride in an amount of 18 g (0.11 mols) is added to the maltodextrin solution. The reaction is allowed to proceed, effectively forming pendent butyrate groups on the pyranose rings of the maltodextrin polymer. This level of derivation results in a degree of substitution (DS) of butyrate group of the hydroxyl groups on the maltodextrin of about 1.

For maltodextrin and other polysaccharides that include three hydroxyl groups per monomeric unit, on average, one of the three hydroxyl groups per glycopyranose monomeric unit becomes substituted with a butyrate group. A maltodextrin polymer having this level of substitution is referred to herein as maltodextrin-butyrate DS 1. As described herein, the DS refers to the average number of reactive groups (including hydroxyl and other reactive groups) per monomeric unit that are substituted with pendent groups comprising hydrocarbon segments.

An increase in the DS can be achieved by incrementally increasing the amount of compound that provides the hydrocarbon segment to the polysaccharide. As another example, butyrylated maltodextrin having a DS of 2.5 is prepared by reacting 10 g of maltodextrin (MW 3000-5000 Da; ~3 mmols) with 0.32 mols butyric anhydride.

The type of hydrocarbon segment present in the groups pendent from the polysaccharide backbone can also influence the hydrophobic properties of the polymer. In one aspect, the implant is formed using a hydrophobic polysaccharide having pendent groups with hydrocarbon segments being short chain branched alkyl group. Exemplary short chain branched alkyl group are branched $C_4$-$C_{10}$ groups. The preparation of a hydrophobic polymer with these types of pendent groups is exemplified by the reaction of maltodextrin with valproic acid/anhydride with maltodextrin (MD-val). The reaction can be carried out to provide a relatively lower degree of substitution of the hydroxyl groups, such as is in the range of 0.5-1.5. Although these polysaccharides have a lower degree of substitution, the short chain branched alkyl group imparts considerable hydrophobic properties to the polysaccharide.

Various synthetic schemes can be used for the preparation of a hydrophobic derivative of a natural degradable polysaccharide. In some modes of preparation, pendent polysaccharide hydroxyl groups are reacted with a compound that includes a hydrocarbon segment and a group that is reactive with the hydroxyl groups. This reaction can provide polysaccharide with pendent groups comprising hydrocarbon segments.

Any suitable chemical group can be coupled to the polysaccharide backbone and provide the polysaccharide with hydrophobic properties, wherein the polysaccharide becomes insoluble in water. Specifically, the pendent group can include one or more atoms selected from carbon (C), hydrogen (H), oxygen (O), nitrogen (N), and sulfur (S).

In some aspects, the pendent group includes a hydrocarbon segment that is a linear, branched, or cyclic $C_2$-$C_{18}$ group. More specifically the hydrocarbon segment includes a $C_2$-$C_{10}$, or a $C_4$-$C_8$, linear, branched, or cyclic group. The hydrocarbon segment can be saturated or unsaturated, and can include alkyl groups or aromatic groups, respectively. The hydrocarbon segment can be linked to the polysaccharide chain via a hydrolyzable bond or a non-hydrolyzable bond.

Degradable polymers of the invention can specifically include polysaccharides such as those described in U.S. Publ. Pat. Application No. 2005/0255142, 2007/0065481, 2007/0218102, 2007/0224247, 2007/0260054, all of which are herein incorporated by reference in their entirety.

In some embodiments, glycerol esters described herein can be used as the continuous phase or the dispersed phase of a colloid, such as an emulsion. By way of example, glycerol esters can be combined with other polymers or components having different physical properties in order to form a colloid. Exemplary components that can serve as the alternate phase (e.g., continuous phase or dispersed phase) to the glycerol ester can include those referred to above in the context of solutes.

In some embodiments, glycerol esters can be combined with particles, such as microparticles, to form a mixture that can be used as an active agent eluting material either by itself or as part of a device such as in the form of a coating. The term "microparticle" is used herein to include nanoparticles, microspheres, nanospheres, microcapsules, nanocapsules, and particles, in general. As such, the term microparticle refers to particles having a variety of internal structure and organizations including homogeneous matrices such as microspheres (and nanospheres) or heterogeneous core-shell matrices (such as microcapsules and nanocapsules), porous particles, multi-layer particles, among others. The term "microparticle" refers generally to particles that have sizes in the range of about 10 nanometers (nm) to about 2 mm (millimeters).

As an example, microparticles including an active agent can be formed and then mixed into a composition including glycerol esters as described herein. The combination of the microparticles and the glycerol ester can then be, for example, injected into a subject for controlled release of the active agent in the microparticles from the resulting depot. While not intending to be bound by theory, it is believed that stability of certain types of active agents in the microparticles can be enhanced through approaches such as this where the active agents are effectively protected against exposure to an environment that may result in degradation or inactivation. For example, proteins, peptides, and nucleic acids can be protected against an aqueous environment.

Microparticles can be formed of various materials including, but not limited to, poly(lactide), poly(glycolide), poly(caprolactone), poly(valerolactone), poly(hydroxybutyrate), poly(lactide-co-glycolide), poly(lactide-co-caprolactone), poly(lactide-co-valerolactone), poly(glycolide-co-caprolactone), poly(glycolide-co-valerolactone), poly(lactide-co-glycolide-co-caprolactone), poly(lactide-co-glycolide-co-valerolactone), poly(lactide)-co-(polyalkylene oxide), poly(lactide-co-glycolide)-co-(polyalkylene oxide), poly(lactide-co-caprolactone)-b-(polyalkylene oxide), poly(lactide-co-glycolide-co-caprolactone)-b-(polyalkylene oxide), poly(lactide)-co-poly(vinylpyrrolidone), poly(lactide-co-glycolide)-co-poly(vinylpyrrolidone), poly(lactide-co-caprolactone)-b-poly(vinylpyrrolidone, polyesters, polyanhydrides, polyorthoesters, polyphosphazenes, polyphosphates, polyphosphoesters, polydioxanones, polyphosphonates, polyhydroxyalkanoates, polycarbonates, polyalkylcarbonates, polyorthocarbonates, polyesteramides, polyamides, polyamines, polypeptides, polyurethanes, polyetheresters, polyalkylene glycols, polyalkylene oxides, polysaccharides, and polyvinyl pyrrolidones. Exemplary microparticles and methods for making the same are described in U.S. Publ. Pat. App. No. 2010/0015240, the content of which is herein incorporated by reference.

It will be appreciated that glycerol esters described herein can be used to form co-polymers. In an embodiment, a copolymer can be formed having formula AB, ABA, or BAB wherein A represents a glycerol ester polymer; and B represents a biocompatible polymer. For example, B can represent at least one selected from the group of poly-lactide-co-glycolide (PLGA), polyethylene glycol (PEG), polyesters, polyurethanes, and polycarbonates. Glycerol esters can be prepared for inclusion in a copolymer by introducing groups making the glycerol ester capable of free-radical polymerization, such as illustrated in Example 22 below, or other groups which would also render the glycerol ester suitable for polymerization.

Active Agents

The term "active agent," refers to an inorganic or organic molecule, which can be synthetic or natural, that causes a biological effect when administered in vivo to an animal, including but not limited to birds and mammals, including humans. A partial list of active agents is provided below. In some embodiments these active agents may be used alone, in other embodiments these active agents may be used in combination with one another. A comprehensive listing of active agents, in addition to information of the water solubility of the active agents, can be found in *The Merck Index*, Fourteenth Edition, Merck & Co. (2006).

Exemplary active agents can include those falling within one or more of the following classes, which include, but are not limited to, ACE inhibitors, actin inhibitors, analgesics, anesthetics, anti-hypertensives, anti polymerases, antisecretory agents, antibiotics, anti-cancer substances, anti-cholinergics, anti-coagulants, anti-convulsants, anti-depressants, anti-emetics, antifungals, anti-glaucoma solutes, antihistamines, antihypertensive agents, anti-inflammatory agents (such as NSAIDs), anti metabolites, antimitotics, antioxidizing agents, anti-parasite and/or anti-Parkinson substances, antiproliferatives (including antiangiogenesis agents), antiprotozoal solutes, anti-psychotic substances, anti-pyretics, antiseptics, anti-spasmodics, antiviral agents, calcium channel blockers, cell response modifiers, chelators, chemotherapeutic agents, dopamine agonists, extracellular matrix components, fibrinolytic agents, free radical scavengers, growth hormone antagonists, hypnotics, immunosuppressive agents, immunotoxins, inhibitors of surface glycoprotein receptors, microtubule inhibitors, miotics, muscle contractants, muscle relaxants, neurotoxins, neurotransmitters, polynucleotides and derivatives thereof, opioids, prostaglandins, remodeling inhibitors, statins, steroids, thrombolytic agents, tranquilizers, vasodilators, and vasospasm inhibitors.

In some aspects the active agent includes an antiproliferative agent. The antiproliferative agent can be an anti-angiogenesis agent. In some aspects the active agent includes an anti-inflammatory agent. In some aspects the active agent includes a cell response modifier. In some aspects the active agent includes an anti-thrombotic agent. In some aspects the active agent includes an immunosuppressive agent.

Cell response modifiers are chemotactic factors such as platelet-derived growth factor (pDGF). Other chemotactic factors include neutrophil-activating protein, monocyte chemoattractant protein, macrophage-inflammatory protein, SIS (small inducible secreted) proteins, platelet factor, platelet basic protein, melanoma growth stimulating activity, epidermal growth factor, transforming growth factor (alpha), fibroblast growth factor, platelet-derived endothelial cell growth factor, insulin-like growth factor, nerve growth factor, vascular endothelial growth factor, bone morphogenic proteins, and bone growth/cartilage-inducing factor (alpha and beta). Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, activin, and DNA that encodes for the production of any of these proteins.

Examples of statins include lovastatin, pravastatin, simvastatin, fluvastatin, atorvastatin, cerivastatin, rosuvastatin, and superstatin.

Examples of steroids include glucocorticoids such as cortisone, hydrocortisone, dexamethasone, betamethasone, prednisone, prednisolone, methylprednisolone, triamcinolone, beclomethasone, fludrocortisone, and aldosterone; sex steroids such as testosterone, dihydrotestosterone, estradiol, diethylstilbestrol, progesterone, and progestins.

The active agent can provide antirestenotic effects, such as antiproliferative, anti-platelet, and/or antithrombotic effects. In some embodiments, the active agent can be selected from anti-inflammatory agents, immunosuppressive agents, cell attachment factors, receptors, ligands, growth factors, antibiotics, enzymes, nucleic acids, and the like. Compounds having antiproliferative effects include, for example, actinomycin D, angiopeptin, c-myc antisense, paclitaxel, taxane, and the like.

Representative examples of active agents having antithrombotic effects include heparin, heparin derivatives, sodium heparin, low molecular weight heparin, hirudin, lysine, prostaglandins, argatroban, forskolin, vapiprost, prostacyclin and prostacyclin analogs, D-phe-pro-arg-chloromethylketone (synthetic antithrombin), dipyridamole, glycoprotein Iib/IIIa platelet membrane receptor antibody, coprotein Iib/IIIa platelet membrane receptor antibody, recombinant hirudin, thrombin inhibitor (such as commercially available from Biogen), chondroitin sulfate, modified dextran, albumin, streptokinase, tissue plasminogen activator (TPA), urokinase, nitric oxide inhibitors, and the like.

The active agent can also be an inhibitor of the GPIIb-IIIa platelet receptor complex, which mediates platelet aggregation. GPIIb/IIIa inhibitors can include monoclonal antibody Fab fragment c7E3, also know as abciximab (ReoPro™), and synthetic peptides or peptidomimetics such as eptifibatide (Integrilin™) or tirofiban (Agrastat™).

The active agent can be an immunosuppressive agent, for example, cyclosporine, CD-34 antibody, everolimus, mycophenolic acid, sirolimus (rapamycin), rapalogs, tacrolimus, and the like.

Additionally, the active agent can be a surface adhesion molecule or cell-cell adhesion molecule. Exemplary cell adhesion molecules or attachment proteins, such as extracellular matrix proteins and peptide sequences for the active sites of fibronectin, laminin, collagen, elastin, vitronectin, tenascin, fibrinogen, thrombospondin, osteopontin, von Willibrand Factor, bone sialoprotein (and active domains thereof), and hydrophilic polymers such as hyaluronic acid, chitosan and methyl cellulose, and other proteins, carbohydrates, and fatty acids. Other cell-cell adhesion molecules include N-cadherin and P-cadherin and active domains thereof.

Devices

In some embodiments, compositions in accordance with embodiments herein can be configured for use as a depot preparation. While many techniques exist for delivering depot preparations, it will be appreciated that one technique involves injecting the composition through a needle, cannula, or the like. The viscosity of the composition can influence the ease with which the composition can be injected through a needle or cannula. The viscosity can be influenced through selection and/or modification of the ester group carbon chains, the number of ester groups on the glycerol backbone, and/or the addition of pendant groups having specific physical properties. In some embodiments, the viscosity of the glycerol ester composition is at least about 100 cP (centipoise) at 37° C. In some embodiments, the viscosity of the glycerol ester composition is less than about 100,000 cP (centipoise) at 37° C. In some embodiments, the viscosity of the glycerol ester composition is between about 1,000 and 30,000 cP (centipoise) at 37° C.

Compositions in accordance with embodiments herein can be configured for use as part of an active agent eluting device. Specific devices can include those having an expandable portion. In some embodiments, the active agent eluting device can include both an expandable portion and a non-expandable portion. An exemplary device is a balloon catheter. Referring now to FIG. 1, a schematic view of an exemplary device is shown in accordance with an embodiment. The device 100 can be, for example, an angioplasty balloon catheter. However, further examples of exemplary devices are described in greater detail below. In this embodiment, the device 100 includes a catheter shaft 102 and a manifold end 105. The device 100 also includes an inflatable balloon 104 disposed around the catheter shaft 102. In FIG. 1, the balloon 104 is shown in an inflated configuration. The catheter shaft 102 can include a channel to convey air through the catheter shaft 102 and to or from the balloon 104, so that the balloon 104 can selectively go from a deflated configuration to the inflated configuration and back again.

Figure 2:
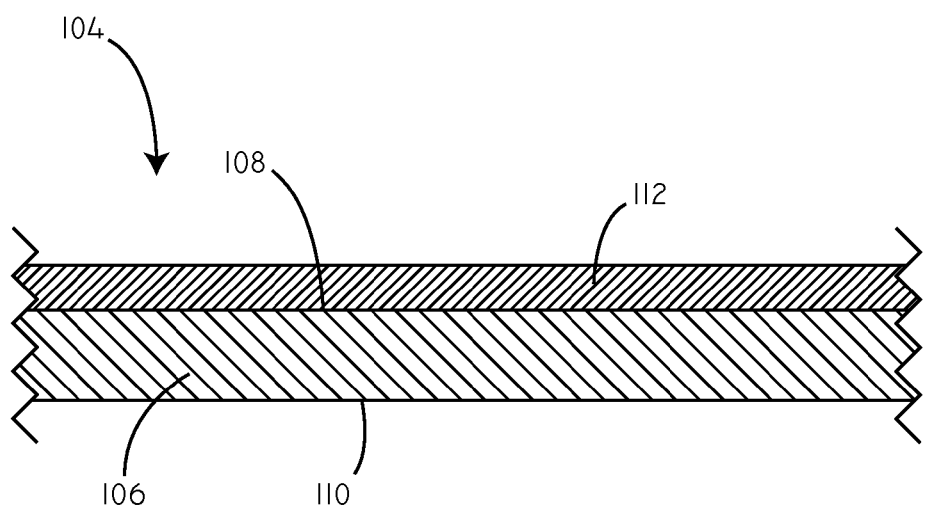
FIG. 2 is a schematic cross-sectional view of a portion of a device in accordance with an embodiment herein.

FIG. 2 shows a schematic cross-sectional view of a portion of the device in accordance with an embodiment herein. Specifically, FIG. 2 shows a cross-sectional view of the expandable balloon 104. The expandable balloon 104 can include a substrate 106 having an inner surface 110 and an outer surface 108. An elution control layer 112 can be disposed on the outer surface 108 of the substrate 106. The elution control layer 112 can include a glycerol ester along with an active agent and, optionally, one or more other components such as polymers.

The substrate 106 can be formed from any material, or combination of materials, capable of expanding, and suitable for use within the body. The one or more material(s) can be based on use of the device. In many embodiments the expandable materials are compliant and flexible materials, such as elastomers (polymers with elastic properties). Exemplary elastomers can be formed from various polymers including polyurethanes and polyurethane copolymers, polyethylene, styrene-butadiene copolymers, polyisoprene, isobutylene-isoprene copolymers (butyl rubber), including halogenated butyl rubber, butadiene-styrene-acrylonitrile copolymers, silicone polymers, fluorosilicone polymers, polycarbonates, polyamides, polyesters, polyvinyl chloride, polyether-polyester copolymers, polyether-polyamide copolymers, and the like. The substrate 106 can be made of a single elastomeric material, or a combination of materials.

The substrate 106 can have a thickness suitable for the desired application and device. For example, the thickness of the substrate 106 can be in the range of about 5 μm to about 100 μm. Exemplary thicknesses for the walls of catheter balloons are in the range of about 5 μm to about 20 μm. The actual thickness of the balloon wall may depend on one or more factors, such as the desired pliability of the balloon, the overall profile of the balloon on the catheter (low profile devices may use thin walled balloons), the pressure rating for the balloon wall, or the expansion properties of the balloon.

The manufacture of expandable substrates is well known in the art, and any suitable process can be carried out to provide the expandable substrate portion of the insertable medical device as described herein. Catheter balloon construction is described in various references, for example, U.S. Pat. Nos. 4,490,421, 5,556,383, 6,210,364, 6,168,748, 6,328,710, and 6,482,348. Molding processes are typically performed for balloon construction. In an exemplary molding process, an extruded polymeric tube is radially and axially expanded at elevated temperatures within a mold having the desired shape of the balloon. The balloon can be subjected to additional treatments following the molding process. For example, the formed balloon can be subjected to additional heating steps to reduce shrinkage of the balloon.

Referring back to FIG. 1, the insertable medical device 100 can also have one or more non-expandable (or inelastic) portions. For example, in a balloon catheter, the catheter shaft 102 portion can be the non-expandable portion. The non-expandable portion can be partially or entirely fabricated from a polymer. Polymers include those formed of synthetic polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, vinylidene difluoride, and styrene. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polydimethylsiloxanes, and polyetherketone.

The non-expandable portion can also be partially or entirely fabricated from a metal. Metals that can be used in medical articles include platinum, gold, or tungsten, as well as other metals such as rhenium, palladium, rhodium, ruthenium, titanium, nickel, and alloys of these metals, such as stainless steel, titanium/nickel, nitinol alloys, cobalt chrome alloys, non-ferrous alloys, and platinum/iridium alloys. One exemplary alloy is MP35.

Figure 3:
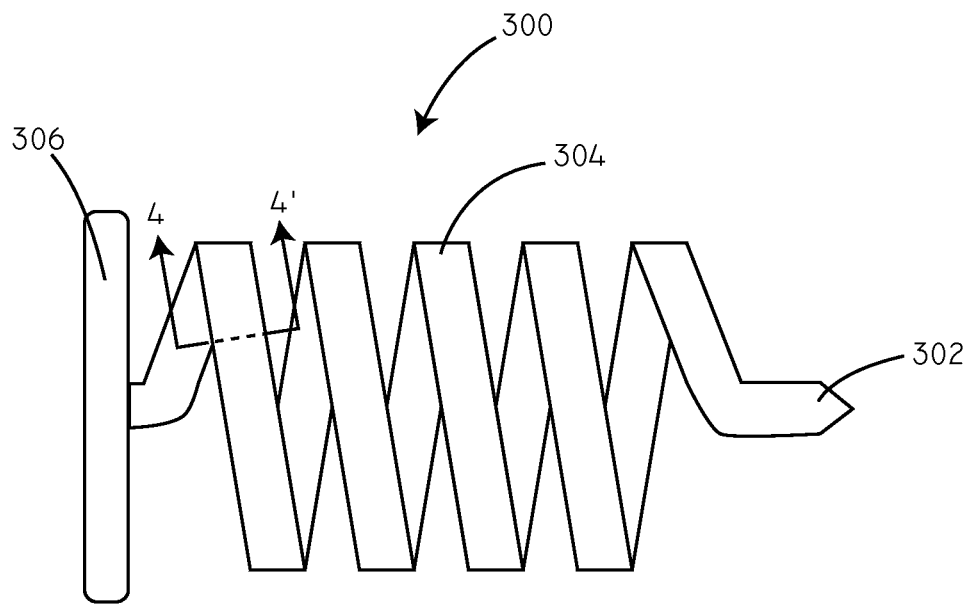
FIG. 3 is a schematic view of a medical device in accordance with an embodiment of the invention.

Referring now to FIG. 3, a schematic view is shown of a medical device 300 in accordance with an embodiment of the invention. In this embodiment, the medical device 300 is an eye screw or eye coil. However, it will be appreciated that other types of medical device are also included within the scope herein. Further examples of medical devices are described below. The medical device 300 includes a tip 302, a coiled body 304, and a cap member 306.

Figure 4:
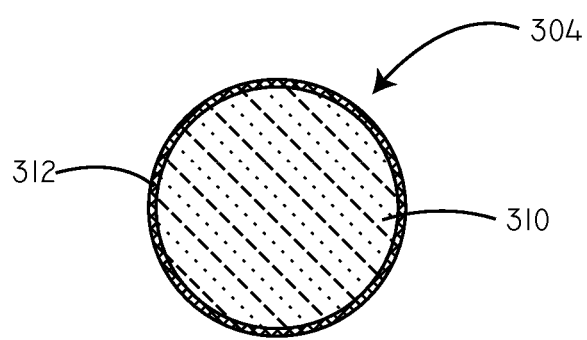
FIG. 4 is a cross-sectional view of the medical device of FIG. 3, as taken along line 4-4'.

Referring now to FIG. 4, a cross-sectional view of the medical device 300 of FIG. 3 is shown as taken along line 4-4' of FIG. 1. In this view, an elution control layer 312 is disposed on a substrate 310. The elution control layer can include a glycerol ester as described herein along with an active agent, and optionally, one or more other components such as polymers. The substrate 310 can include various materials as described more fully below, including but not limited to, metals, ceramics, polymers, glasses, and the like.

Compositions herein can also be used in conjunction with other devices including both implantable devices and non-implantable medical devices. Embodiments of the invention can include and can be used with implantable, or transitorily implantable, devices including, but not limited to, vascular devices such as grafts (e.g., abdominal aortic aneurysm grafts, etc.), stents (e.g., self-expanding stents typically made from nitinol, balloon-expanded stents typically prepared from stainless steel, degradable coronary stents, etc.), catheters (including arterial, intravenous, blood pressure, stent graft, etc.), valves (e.g., polymeric or carbon mechanical valves, tissue valves, valve designs including percutaneous, sewing cuff, and the like), embolic protection filters (including distal protection devices), vena cava filters, aneurysm exclusion devices, artificial hearts, cardiac jackets, and heart assist devices (including left ventricle assist devices), implantable defibrillators, electro-stimulation devices and leads (including pacemakers, lead adapters and lead connectors), implanted medical device power supplies (e.g., batteries, etc.), peripheral cardiovascular devices, atrial septal defect closures, left atrial appendage filters, valve annuloplasty devices (e.g., annuloplasty rings), mitral valve repair devices, vascular intervention devices, ventricular assist pumps, and vascular access devices (including parenteral feeding catheters, vascular access ports, central venous access catheters); surgical devices such as sutures of all types, staples, anastomosis devices (including anastomotic closures), suture anchors, hemostatic barriers, screws, plates, clips, vascular implants, tissue scaffolds, cerebro-spinal fluid shunts, shunts for hydrocephalus, drainage tubes, catheters including thoracic cavity suction drainage catheters, abscess drainage catheters, biliary drainage products, and implantable pumps; orthopedic devices such as joint implants, acetabular cups, patellar buttons, bone repair/augmentation devices, spinal devices (e.g., vertebral disks and the like), bone pins, cartilage repair devices, and artificial tendons; dental devices such as dental implants and dental fracture repair devices; drug delivery devices such as drug delivery pumps, implanted drug infusion tubes, drug infusion catheters, and intravitreal drug delivery devices; ophthalmic devices including orbital implants, glaucoma drain shunts and intraocular lenses; urological devices such as penile devices (e.g., impotence implants), sphincter, urethral, prostate, and bladder devices (e.g., incontinence devices, benign prostate hyperplasia management devices, prostate cancer implants, etc.), urinary catheters including indwelling ("Foley") and non-indwelling urinary catheters, and renal devices; synthetic prostheses such as breast prostheses and artificial organs (e.g., pancreas, liver, lungs, heart, etc.); respiratory devices including lung catheters; neurological devices such as neurostimulators, neurological catheters, neurovascular balloon catheters, neuro-aneurysm treatment coils, and neuropatches; ear nose and throat devices such as nasal buttons, nasal and airway splints, nasal tampons, ear wicks, ear drainage tubes, tympanostomy vent tubes, otological strips, laryngectomy tubes, esophageal tubes, esophageal stents, laryngeal stents, salivary bypass tubes, and tracheostomy tubes; biosensor devices including glucose sensors, cardiac sensors, intra-arterial blood gas sensors; oncological implants; and pain management implants.

Classes of non-implantable devices can include dialysis devices and associated tubing, catheters, membranes, and grafts; autotransfusion devices; vascular and surgical devices including atherectomy catheters, angiographic catheters, intraaortic balloon pumps, intracardiac suction devices, blood pumps, blood oxygenator devices (including tubing and membranes), blood filters, blood temperature monitors, hemoperfusion units, plasmapheresis units, transition sheaths, dialators, intrauterine pressure devices, clot extraction catheters, percutaneous transluminal angioplasty catheters, electrophysiology catheters, breathing circuit connectors, stylets (vascular and non-vascular), coronary guide wires, peripheral guide wires; dialators (e.g., urinary, etc.); surgical instruments (e.g. scalpels and the like); endoscopic devices (such as endoscopic surgical tissue extractors, esophageal stethoscopes); and general medical and medically related devices including blood storage bags, umbilical tape, membranes, gloves, surgical drapes, wound dressings, wound management devices, needles, percutaneous closure devices, transducer protectors, pessary, uterine bleeding patches, PAP brushes, clamps (including bulldog clamps), cannulae, cell culture devices, materials for in vitro diagnostics, chromatographic support materials, infection control devices, colostomy bag attachment devices, birth control devices; disposable temperature probes; and pledgets.

In some aspects, embodiments of the invention can include and be utilized in conjunction with ophthalmic devices. Suitable ophthalmic devices in accordance with these aspects can provide active agent to any desired area of the eye. In some aspects, the devices can be utilized to deliver active agent to an anterior segment of the eye (in front of the lens), and/or a posterior segment of the eye (behind the lens). Suitable ophthalmic devices can also be utilized to provide active agent to tissues in proximity to the eye, when desired.

In some aspects, embodiments of the invention can be utilized in conjunction with ophthalmic devices configured for placement at an external or internal site of the eye. Suitable external devices can be configured for topical administration of active agent. Such external devices can reside on an external surface of the eye, such as the cornea (for example, contact lenses) or bulbar conjunctiva. In some embodiments, suitable external devices can reside in proximity to an external surface of the eye.

The present invention may be better understood with reference to the following examples. These examples are intended to be representative of specific embodiments of the invention, and are not intended as limiting the scope of the invention.

EXAMPLES

The necessary reagents used to synthesize the following examples are all commercially available from a variety of sources. Polyglycerols #310, #500 and #750 were available as samples from the supplier, Sakamoto Yakuhin Kogyo Co., Ltd. (Japan). The fatty acids: hexanoic acid, octanoic acid, decanoic acid, dodecanoic acid, and oleic acid were available through Sigma Aldrich (St. Louis, Mo.). Solvents used in the various reactions we all purchased through VWR (West Chester, Pa.). Additional reagents such as N,N-dimethylaminopyridine, N-hydroxysuccinimide, N,N-diisopropylcarbodiimide, EDC HCl, and sulfuric acid were all purchased from Sigma Aldrich (St. Louis, Mo.).

Example 1

Synthesis of Tetraglycerol Hexyloctanoate (Method I)

Into a 250 mL vessel, tetraglycerol (5.0 g, 15.91 mmol) was added and dissolved into anhydrous DMSO (50 mL). Octanoic acid (15.12 mL, 95.44 mmol) was also dissolved into the reaction mixture which was stirred magnetically at room temperature for one hour to fully dissolve the reagents. N,N-dimethylaminopyridine (0.194 g, 1.59 mmol) and N-hydroxysuccinimide (0.183 g, 1.59 mmol) were both dissolved in the solution. When the catalysts were fully dissolved, N,N-diisopropylcarbodiimide (15.0 mL, 97.03 mmol) was pipetted into the vessel and was sealed to keep the reaction dry. The reaction proceeded overnight at 55° C. The solution was dialyzed in SpectraPor7 MWCO 1000 dialysis tubing to remove the DMSO and unreacted monomer. The polymer crashed out in water into a thick white liquid. After 3 days of dialysis, the solution was placed into a reparatory funnel and the organic portion was dissolved into chloroform. The water layer was removed and the organic layer was dried with sodium sulfate. The solvent was stripped via rotoevaporation to leave a clear thick liquid product. NMR analysis supported full conversion of hydroxyl groups to the octanoic esters.

Example 2

Synthesis of Tetraglycerol Hexylhexanoate (Method I)

Into a 250 mL vessel, tetraglycerol (5.0 g, 15.91 mmol) was added and dissolved into anhydrous DMSO (50 mL). Hexanoic acid (11.96 mL, 95.44 mmol) was also dissolved into the reaction mixture which was stirred magnetically at room temperature for one hour to fully dissolve the reagents. N,N-dimethylaminopyridine (0.194 g, 1.59 mmol) and N-hydroxysuccinimide (0.183 g, 1.59 mmol) were both dissolved in the solution. When the catalysts were fully dissolved, N,N-diisopropylcarbodiimide (15.0 mL, 97.03 mmol) was pipetted into the vessel and was sealed to keep the reaction dry. The reaction proceeded overnight at 55° C. The solution was dialyzed in SpectraPor7 MWCO 1000 dialysis tubing to remove the DMSO and unreacted monomer. The polymer crashed out in water into a thick white liquid. After 3 days of dialysis, the solution was placed into a separatory funnel and the organic portion was dissolved into chloroform. The water layer was removed and the organic layer was dried with sodium sulfate. The solvent was stripped via rotoevaporation to leave a clear thick liquid product. NMR analysis supported full conversion of hydroxyl groups to the hexanoic esters.

Example 3

Synthesis of Hexaglycerol Octyloctanoate (Method I)

Into a 250 mL vessel, hexaglycerol (5.0 g, 10.81 mmol) was added and dissolved into anhydrous DMSO (50 mL). Octanoic acid (13.71 mL, 86.49 mmol) was also dissolved into the reaction mixture which was stirred magnetically at room temperature for one hour to fully dissolve the reagents. N,N-dimethylaminopyridine (0.132 g, 1.08 mmol) and N-hydroxysuccinimide (0.124 g, 1.08 mmol) were both dissolved in the solution. When the catalysts were fully dissolved, N,N-diisopropylcarbodiimide (13.54 mL, 87.57 mmol) was pipetted into the vessel and was sealed to keep the reaction dry. The reaction proceeded overnight at 55° C. The solution was dialyzed in SpectraPor7 MWCO 1000 dialysis tubing to remove the DMSO and unreacted monomer. The polymer crashed out in water into a thick white liquid. After 3 days of dialysis, the solution was placed into a separatory funnel and the organic portion was dissolved into chloroform. The water layer was removed and the organic layer was dried with

Example 4

Synthesis of Hexaglycerol Octyloctanoate (Method I)

Into a 250 mL vessel, hexaglycerol (5.0 g, 10.81 mmol) was added and dissolved into anhydrous DMSO (50 mL). Hexanoic acid (10.84 mL, 86.49 mmol) was also dissolved into the reaction mixture which was stirred magnetically at room temperature for one hour to fully dissolve the reagents. N,N-dimethylaminopyridine (0.132 g, 1.08 mmol) and N-hydroxysuccinimide (0.124 g, 1.08 mmol) were both dissolved in the solution. When the catalysts were fully dissolved, N,N-diisopropylcarbodiimide (13.54 mL, 87.57 mmol) was pipetted into the vessel and was sealed to keep the reaction dry. The reaction proceeded overnight at 55° C. The solution was dialyzed in SpectraPor7 MWCO 1000 dialysis tubing to remove the DMSO and unreacted monomer. The polymer crashed out in water into a thick white liquid. After 3 days of dialysis, the solution was placed into a separatory funnel and the organic portion was dissolved into chloroform. The water layer was removed and the organic layer was dried with sodium sulfate. The solvent was stripped via rotoevaporation to leave a clear thick liquid product. NMR analysis supported full conversion of hydroxyl groups to the hexanoic esters.

Example 5

Synthesis of Decaglycerol Dodecyloctanoate (Method I)

Into a 250 mL vessel, decaglycerol (5.0 g, 6.59 mmol) was added and dissolved into anhydrous DMSO (50 mL). Octanoic acid (12.53 mL, 79.07 mmol) was also dissolved into the reaction mixture which was stirred magnetically at room temperature for one hour to fully dissolve the reagents. N,N-dimethylaminopyridine (0.081 g, 0.66 mmol) and N-hydroxysuccinimide (0.076 g, 0.66 mmol) were both dissolved in the solution. When the catalysts were fully dissolved, N,N-diisopropylcarbodiimide (12.33 mL, 79.73 mmol) was pipetted into the vessel and was sealed to keep the reaction dry. The reaction proceeded overnight at 55° C. The solution was dialyzed in SpectraPor7 MWCO 1000 dialysis tubing to remove the DMSO and unreacted monomer. The polymer crashed out in water into a thick white liquid. After 3 days of dialysis, the solution was placed into a separatory funnel and the organic portion was dissolved into chloroform. The water layer was removed and the organic layer was dried with sodium sulfate. The solvent was stripped via rotoevaporation to leave a clear thick liquid product. NMR analysis supported full conversion of hydroxyl groups to the octanoic esters.

Example 6

Synthesis of Decaglycerol Dodecylhexanoate (Method I)

Into a 250 mL vessel, decaglycerol (5.0 g, 6.59 mmol) was added and dissolved into anhydrous DMSO (50 mL). Hexanoic acid (9.91 mL, 79.07 mmol) was also dissolved into the reaction mixture which was stirred magnetically at room temperature for one hour to fully dissolve the reagents. N,N-dimethylaminopyridine (0.081 g, 0.66 mmol) and N-hydroxysuccinimide (0.076 g, 0.66 mmol) were both dissolved in the solution. When the catalysts were fully dissolved, N,N-diisopropylcarbodiimide (12.33 mL, 79.73 mmol) was pipetted into the vessel and was sealed to keep the reaction dry. The reaction proceeded overnight at 55° C. The solution was dialyzed in SpectraPor7 MWCO 1000 dialysis tubing to remove the DMSO and unreacted monomer. The polymer crashed out in water into a thick white liquid. After 3 days of dialysis, the solution was placed into a reparatory funnel and the organic portion was dissolved into chloroform. The water layer was removed and the organic layer was dried with sodium sulfate. The solvent was stripped via rotoevaporation to leave a clear thick liquid product. NMR analysis supported full conversion of hydroxyl groups to the hexanoic esters.

Example 7

Synthesis of Tetraglycerol Hexyloctanoate (Method II)

Into a 250 mL vessel, tetraglycerol (5.0 g, 15.91 mmol) was added and dissolved into anhydrous THF (50 mL). Octanoic acid (15.12 mL, 95.44 mmol) was also dissolved into the reaction mixture which was stirred magnetically at room temperature for one hour to fully dissolve the reagents. N,N-dimethylaminopyridine (0.194 g, 1.59 mmol) and N-hydroxysuccinimide (0.183 g, 1.59 mmol) were both dissolved in the solution. When the catalysts were fully dissolved, N,N-diisopropylcarbodiimide (15.0 mL, 97.03 mmol) was pipetted into the vessel and was sealed to keep the reaction dry. The reaction proceeded overnight at 55° C. The solution was stripped of THF via rotoevaporation and redissolved into chloroform. The organic layer was washed 2× with sodium bicarbonate buffer and 2× with deionized water to remove unreacted starting materials. The chloroform was removed to yield a clear viscous liquid. NMR analysis supported full conversion of hydroxyl groups to the octanoic esters.

Example 8

Synthesis of Tetraglycerol Hexylhexanoate (Method II)

Into a 250 mL vessel, tetraglycerol (5.0 g, 15.91 mmol) was added and dissolved into anhydrous THF (50 mL). Hexanoic acid (11.96 mL, 95.44 mmol) was also dissolved into the reaction mixture which was stirred magnetically at room temperature for one hour to fully dissolve the reagents. N,N-dimethylaminopyridine (0.194 g, 1.59 mmol) and N-hydroxysuccinimide (0.183 g, 1.59 mmol) were both dissolved in the solution. When the catalysts were fully dissolved, N,N-diisopropylcarbodiimide (15.0 mL, 97.03 mmol) was pipetted into the vessel and was sealed to keep the reaction dry. The reaction proceeded overnight at 55° C. The solution was stripped of THF via rotoevaporation and redissolved into chloroform. The organic layer was washed 2× with sodium bicarbonate buffer and 2× with deionized water to remove unreacted starting materials. The chloroform was removed to yield a clear viscous liquid. NMR analysis supported full conversion of hydroxyl groups to the hexanoic esters.

Example 9

Synthesis of Hexaglycerol Octyloctanoate (Method II)

Into a 250 mL vessel, hexaglycerol (5.0 g, 10.81 mmol) was added and dissolved into anhydrous THF (50 mL).

Octanoic acid (13.71 mL, 86.49 mmol) was also dissolved into the reaction mixture which was stirred magnetically at room temperature for one hour to fully dissolve the reagents. N,N-dimethylaminopyridine (0.132 g, 1.08 mmol) and N-hydroxysuccinimide (0.124 g, 1.08 mmol) were both dissolved in the solution. When the catalysts were fully dissolved, N,N-diisopropylcarbodiimide (13.54 mL, 87.57 mmol) was pipetted into the vessel and was sealed to keep the reaction dry. The reaction proceeded overnight at 55° C. The solution was stripped of THF via rotoevaporation and redissolved into chloroform. The organic layer was washed 2× with sodium bicarbonate buffer and 2× with deionized water to remove unreacted starting materials. The chloroform was removed to yield a clear viscous liquid. NMR analysis supported full conversion of hydroxyl groups to the octanoic esters.

Example 10

Synthesis of Hexaglycerol Octyloctanoate (Method II)

Into a 250 mL vessel, hexaglycerol (5.0 g, 10.81 mmol) was added and dissolved into anhydrous THF (50 mL). Hexanoic acid (10.84 mL, 86.49 mmol) was also dissolved into the reaction mixture which was stirred magnetically at room temperature for one hour to fully dissolve the reagents. N,N-dimethylaminopyridine (0.132 g, 1.08 mmol) and N-hydroxysuccinimide (0.124 g, 1.08 mmol) were both dissolved in the solution. When the catalysts were fully dissolved, N,N-diisopropylcarbodiimide (13.54 mL, 87.57 mmol) was pipetted into the vessel and was sealed to keep the reaction dry. The reaction proceeded overnight at 55° C. The solution was stripped of THF via rotoevaporation and redissolved into chloroform. The organic layer was washed 2× with sodium bicarbonate buffer and 2× with deionized water to remove unreacted starting materials. The chloroform was removed to yield a clear viscous liquid. NMR analysis supported full conversion of hydroxyl groups to the hexanoic esters.

Example 11

Synthesis of Decaglycerol Dodecyloctanoate (Method II)

Into a 250 mL vessel, decaglycerol (5.0 g, 6.59 mmol) was added and dissolved into anhydrous THF (50 mL). Octanoic acid (12.53 mL, 79.07 mmol) was also dissolved into the reaction mixture which was stirred magnetically at room temperature for one hour to fully dissolve the reagents. N,N-dimethylaminopyridine (0.081 g, 0.66 mmol) and N-hydroxysuccinimide (0.076 g, 0.66 mmol) were both dissolved in the solution. When the catalysts were fully dissolved, N,N-diisopropylcarbodiimide (12.33 mL, 79.73 mmol) was pipetted into the vessel and was sealed to keep the reaction dry. The reaction proceeded overnight at 55° C. The solution was stripped of THF via rotoevaporation and redissolved into chloroform. The organic layer was washed 2× with sodium bicarbonate buffer and 2× with deionized water to remove unreacted starting materials. The chloroform was removed to yield a clear viscous liquid. NMR analysis supported full conversion of hydroxyl groups to the octanoic esters.

Example 12

Synthesis of Decaglycerol Dodecylhexanoate (Method II)

Into a 250 mL vessel, decaglycerol (5.0 g, 6.59 mmol) was added and dissolved into anhydrous THF (50 mL). Hexanoic acid (9.91 mL, 79.07 mmol) was also dissolved into the reaction mixture which was stirred magnetically at room temperature for one hour to fully dissolve the reagents. N,N-dimethylaminopyridine (0.081 g, 0.66 mmol) and N-hydroxysuccinimide (0.076 g, 0.66 mmol) were both dissolved in the solution. When the catalysts were fully dissolved, N,N-diisopropylcarbodiimide (12.33 mL, 79.73 mmol) was pipetted into the vessel and was sealed to keep the reaction dry. The reaction proceeded overnight at 55° C. The solution was stripped of THF via rotoevaporation and redissolved into chloroform. The organic layer was washed 2× with sodium bicarbonate buffer and 2× with deionized water to remove unreacted starting materials. The chloroform was removed to yield a clear viscous liquid. NMR analysis supported full conversion of hydroxyl groups to the hexanoic esters.

Example 13

Synthesis of Tetraglycerol Octylhexanoate (Method III)

Into a 250 mL vessel, tetraglycerol (5.0 g, 15.91 mmol) was added and dissolved into anhydrous THF (50 mL). Octanoic acid (15.12 mL, 95.44 mmol) was also dissolved into the reaction mixture which was stirred magnetically at room temperature for one hour to fully dissolve the reagents. N,N-dimethylaminopyridine (0.194 g, 1.59 mmol) was dissolved in the solution. When the catalyst was fully dissolved, EDC HCl (18.32 g, 95.6 mmol) was added into the vessel and was sealed to keep the reaction dry. The reaction proceeded overnight at 55° C. The solution was stripped of THF via rotoevaporation and redissolved into chloroform. The organic layer was washed 2× with sodium bicarbonate buffer and 2× with deionized water to remove unreacted starting materials. The chloroform was removed to yield a clear viscous liquid. NMR analysis supported full conversion of hydroxyl groups to the octanoic esters.

Example 14

Synthesis of Tetraglycerol Hexylhexanoate (Method III)

Into a 250 mL vessel, tetraglycerol (5.0 g, 15.91 mmol) was added and dissolved into anhydrous THF (50 mL). Hexanoic acid (11.96 mL, 95.44 mmol) was also dissolved into the reaction mixture which was stirred magnetically at room temperature for one hour to fully dissolve the reagents. N,N-dimethylaminopyridine (0.194 g, 1.59 mmol) was dissolved in the solution. When the catalyst was fully dissolved, EDC HCl (18.32 g, 95.6 mmol) was added into the vessel and was sealed to keep the reaction dry. The reaction proceeded overnight at 55° C. The solution was stripped of THF via rotoevaporation and redissolved into chloroform. The organic layer was washed 2× with sodium bicarbonate buffer and 2× with deionized water to remove unreacted starting materials. The chloroform was removed to yield a clear viscous liquid. NMR analysis supported full conversion of hydroxyl groups to the hexanoic esters.

Example 15

Synthesis of Hexaglycerol Octyloctanoate (Method III)

Into a 250 mL vessel, hexaglycerol (5.0 g, 10.81 mmol) was added and dissolved into anhydrous THF (50 mL).

Octanoic acid (13.71 mL, 86.49 mmol) was also dissolved into the reaction mixture which was stirred magnetically at room temperature for one hour to fully dissolve the reagents. N,N-dimethylaminopyridine (0.132 g, 1.08 mmol) was dissolved in the solution. When the catalyst was fully dissolved, EDC HCl (16.6 g, 86.6 mmol) was pipetted into the vessel and was sealed to keep the reaction dry. The reaction proceeded overnight at 55° C. The solution was stripped of THF via rotoevaporation and redissolved into chloroform. The organic layer was washed 2× with sodium bicarbonate buffer and 2× with deionized water to remove unreacted starting materials. The chloroform was removed to yield a clear viscous liquid. NMR analysis supported full conversion of hydroxyl groups to the octanoic esters.

Example 16

Synthesis of Hexaglycerol Octyloctanoate (Method III)

Into a 250 mL vessel, hexaglycerol (5.0 g, 10.81 mmol) was added and dissolved into anhydrous THF (50 mL). Hexanoic acid (10.84 mL, 86.49 mmol) was also dissolved into the reaction mixture which was stirred magnetically at room temperature for one hour to fully dissolve the reagents. N,N-dimethylaminopyridine (0.132 g, 1.08 mmol) was dissolved in the solution. When the catalysts were fully dissolved, EDC HCl (16.6 g, 86.6 mmol) was pipetted into the vessel and was sealed to keep the reaction dry. The reaction proceeded overnight at 55° C. The solution was stripped of THF via rotoevaporation and redissolved into chloroform. The organic layer was washed 2× with sodium bicarbonate buffer and 2× with deionized water to remove unreacted starting materials. The chloroform was removed to yield a clear viscous liquid. NMR analysis supported full conversion of hydroxyl groups to the hexanoic esters.

Example 17

Synthesis of Decaglycerol Dodecyldodecanoate (Method II)

Into a 250 mL vessel, decaglycerol (5.0 g, 6.59 mmol) was added and dissolved into anhydrous THF (50 mL). Dodecanoic acid (15.84 g, 79.07 mmol) was also dissolved into the reaction mixture which was stirred magnetically at room temperature for one hour to fully dissolve the reagents. N,N-dimethylaminopyridine (0.081 g, 0.66 mmol) and N-hydroxysuccinimide (0.076 g, 0.66 mmol) were both dissolved in the solution. When the catalysts were fully dissolved, N,N-diisopropylcarbodiimide (12.33 mL, 79.73 mmol) was pipetted into the vessel and was sealed to keep the reaction dry. The reaction proceeded overnight at 55° C. The solution was stripped of THF via rotoevaporation and redissolved into chloroform. The organic layer was washed 2× with sodium bicarbonate buffer and 2× with deionized water to remove unreacted starting materials. The chloroform was removed to yield a white waxy precipitate. NMR analysis supported full conversion of hydroxyl groups to the dodecanoic esters.

Example 18

Synthesis of Decaglycerol Dodecyldecanoate (Method II)

Into a 250 mL vessel, decaglycerol (5.0 g, 6.59 mmol) was added and dissolved into anhydrous THF (50 mL). Decanoic acid (13.62 g, 79.07 mmol) was also dissolved into the reaction mixture which was stirred magnetically at room temperature for one hour to fully dissolve the reagents. N,N-dimethylaminopyridine (0.081 g, 0.66 mmol) and N-hydroxysuccinimide (0.076 g, 0.66 mmol) were both dissolved in the solution. When the catalysts were fully dissolved, N,N-diisopropylcarbodiimide (12.33 mL, 79.73 mmol) was pipetted into the vessel and was sealed to keep the reaction dry. The reaction proceeded overnight at 55° C. The solution was stripped of THF via rotoevaporation and redissolved into chloroform. The organic layer was washed 2× with sodium bicarbonate buffer and 2× with deionized water to remove unreacted starting materials. The chloroform was removed to yield a white waxy precipitate with a melting point around room temperature. NMR analysis supported full conversion of hydroxyl groups to the decanoic esters.

Example 19

Synthesis of Decaglycerol Dodecyloleate (Method II)

Into a 250 mL vessel, decaglycerol (5.0 g, 6.59 mmol) was added and dissolved into anhydrous THF (50 mL). Oleic acid (25.09 mL, 79.07 mmol) was also dissolved into the reaction mixture which was stirred magnetically at room temperature for one hour to fully dissolve the reagents. N,N-dimethylaminopyridine (0.081 g, 0.66 mmol) and N-hydroxysuccinimide (0.076 g, 0.66 mmol) were both dissolved in the solution. When the catalysts were fully dissolved, N,N-diisopropylcarbodiimide (12.33 mL, 79.73 mmol) was pipetted into the vessel and was sealed to keep the reaction dry. The reaction proceeded overnight at 55° C. The solution was stripped of THF via rotoevaporation and redissolved into chloroform. The organic layer was washed 2× with sodium bicarbonate buffer and 2× with deionized water to remove unreacted starting materials. The chloroform was removed to yield a clear liquid. NMR analysis supported full conversion of hydroxyl groups to the oleic esters.

Example 20

Synthesis of Decaglycerol Dodecyldodecanoate (Method IV)

Into a 250 mL vessel, decaglycerol (5.0 g, 6.59 mmol) was added and dissolved into anhydrous THF (50 mL). Dodecanoic acid (15.84 g, 79.07 mmol) was also dissolved into the reaction mixture which was stirred magnetically at room temperature for one hour to fully dissolve the reagents. Sulfuric acid (200 uL, 3.75 mmol) was pipetted into the vessel and was sealed to keep the reaction dry. The reaction was brought to reflux set up with a condenser in a heating mantle equipped with a magnetic stir plate. The reaction was left to proceed overnight (16 h). The solution was stripped of THF via rotoevaporation and redissolved into chloroform. The organic layer was washed 2× with sodium bicarbonate buffer and 2× with deionized water to remove unreacted starting materials. The chloroform was removed to yield a white waxy precipitate.

Example 21

Synthesis of Decaglycerol Dodecyldecanoate (Method IV)

Into a 250 mL vessel, decaglycerol (5.0 g, 6.59 mmol) was added and dissolved into anhydrous THF (50 mL). Decanoic acid (13.62 g, 79.07 mmol) was also dissolved into the reaction mixture which was stirred magnetically at room temperature for one hour to fully dissolve the reagents. Sulfuric acid (200 uL, 3.75 mmol) was pipetted into the vessel and was sealed to keep the reaction dry. The reaction was brought to reflux set up with a condenser in a heating mantle equipped with a magnetic stir plate. The reaction was left to proceed overnight (16 h). The solution was then stripped of THF via rotoevaporation and redissolved into chloroform. The organic layer was washed 2× with sodium bicarbonate buffer and 2× with deionized water to remove unreacted starting materials. The chloroform was removed to yield a white waxy precipitate with a melting point around room temperature.

Example 22

Synthesis of Esterified Product for Free-Radical Polymerization

Into a reaction flask fitted with an overhead stirrer, 10 mM decaglycerol is added through a funnel. The solvent DMF is added subsequently to dissolve the material. To protect both of the primary alcohols, 20 mM trityl chloride is added. DMAP is added in catalytic amounts to help reaction yields. The solution is stirred for 12 hours at room temperature to selectively protect the primary alcohols. Once the tritylated product is isolated from the reaction mixture, it is redissolved into anhydrous THF and heated to 50° C. to solubilize the material. Approximately 100 mM of octanoic acid is added to the flask that is magnetically stirring. Catalytic amounts of DMAP and NHS can be added to increase the rate of esterification. N,N'-diisopropylcarbodiimide is added at 101 mM to be used as the base in the reaction. The final product is chilled to crystallize out the diisopropylurea byproduct crystals which are then removed by filtration. The THF is removed by rotoevaporation to yield the trityl-protected decaester. A solution of formic acid and ether is used to cleave the trityl groups in roughly 60 minutes with decent yield. After isolating the unprotected product, the reagent is solubilized in dichloromethane. Approximately 20 mM methacrylic anhydride is added with 20 mM 1-methylimidazole to create the primary alcohol methacrylate esters after 1 hour at room temperature. This is purified to yield an esterified product capable of free-radical polymerization.

Example 23

Synthesis of Esterified Product Capable of Nucleophilic Reaction with a Hydrazide-Reactive Group Into a reaction flask fitted with an overhead stirrer, 10 mM decaglycerol is added through a funnel. The solvent DMF is added subsequently to dissolve the material. To protect both of the primary alcohols, 20 mM trityl chloride is added. DMAP is added in catalytic amounts to help reaction yields. The solution is stirred for 12 hours at room temperature to selectively protect the primary alcohols. Once the tritylated product is isolated from the reaction mixture, it is redissolved into anhydrous THF and heated to 50° C. to solubilize the material. Approximately 100 mM of octanoic acid is added to the flask that is magnetically stirring. Catalytic amounts of DMAP and NHS could be added to increase the rate of esterification. N,N'-diisopropylcarbodiimide is added at 101 mM to be used as the base in the reaction. The final product is chilled to crystallize out the diisopropylurea byproduct crystals which are then removed by filtration. The THF can be removed by rotoevaporation to yield the trityl-protected decaester. A solution of formic acid and ether is used to cleave the trityl groups in roughly 60 minutes with decent yield. After isolating the unprotected product, the reagent is solubilized in dichloromethane. Approximately 20 mM 1,1'-carbonyldiimidazole is added with 1000 mM hydrazine to convert the free primary alcohols to hydrazide groups after 2 hours at room temperature. This is purified to yield an esterified product capable of nucleophilic reaction with a hydrazide-reactive group.

Example 24

Formation of Glycerol Ester Polymer

Into a reaction flask fitted with an overhead stirrer, the decyloctanoate decaglycerol bearing two free primary hydroxyl groups (Example 22) is dissolved into degassed dimethylsulfoxide (DMSO) at 5% solids. Additionally, catalytic amounts of N, N,N',N'-tetramethylenediamine (TEMED) is added as an oxygen scavenger. The initiator ammonium persulfate is dissolved in a 10% wt. solution and added in the appropriate amounts to control the molecular weight of the polymer. The flask can remain at room temperature or be heated to promote polymerization. The polymerization should proceed overnight. Once polymerization occurs, the product is precipitated or dialyzed in water to remove solvent and remaining initiator. The final product is a hydrophobic polymer.

Example 25

Formation of Glycerol Ester Polymer

Into a reaction flask fitted with an overhead stirrer, the decyloctanoate decaglycerol bearing two free hydrazide groups (Example 23) is dissolved into degassed dimethylsulfoxide (DMSO) at 5% solids. 1,1'-carbonyldiimidazole is added in equimolar concentrations to the oligomer in order to crosslink the hydrazide groups through a urea linkage. The reaction will proceed relatively quickly. Once polymerization occurs, the product is precipitated or dialyzed in water to remove solvent and remaining initiator. The final product is a hydrophobic polymer.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

The invention claimed is:

1. A composition comprising:
   a glycerol ester polymer comprising at least one polymer selected from the group consisting of tetraglycerol hexyloctanoate, tetraglycerol hexylhexanoate, hexaglycerol octyloctanoate, decaglycerol dodecylhexanoate, tetraglycerol octylhexanoate, decaglycerol dodecyldodecanoate, and decaglycerol dodecyldecanoate;
   an active agent dispersed within the glycerol ester polymer;
   wherein the composition is configured to have the active agent eluted from the glycerol ester polymer under physiologic conditions.

2. The composition of claim 1, the composition configured to elute the active agent in response to degradation of the glycerol ester polymer.

3. The composition of claim 2, wherein degradation of the glycerol ester polymer takes place in vivo.

4. The composition of claim 1, wherein the glycerol ester polymer has a molecular weight of greater than or equal to 5,000.

5. The composition of claim 1, wherein the glycerol ester polymer has a melting temperature (Tm) of greater than about 25 degrees Celsius and less than about 37 degrees Celsius.

6. The composition of claim 1, wherein the glycerol ester polymer comprises an ester group including a carbon chain comprising greater than or equal to 6 carbon atoms.

7. The composition of claim 1, wherein the glycerol ester polymer comprises an ester group comprising a pendant active agent or proagent as part of the ester group.

8. The composition of claim 1, wherein the glycerol ester polymer comprises an ester group comprising a covalently bound anti-inflammatory agent.

9. The composition of claim 1, wherein the glycerol ester glycerol comprises an ester group comprising a salicylate.

10. The composition of claim 1, wherein the glycerol ester polymer is covalently bonded to a surface of a substrate through a linking group.

11. The composition of claim 10, wherein the linking group comprises a silane compound.

12. The composition of claim 1, wherein the glycerol ester polymer is covalently bonded to a surface of a substrate through a photoreactive group.

13. The composition of claim 1, wherein the glycerol ester polymer is cross-linked with a cross-linking agent.

14. The composition of claim 1, further comprising a biocompatible polymer dispersed within the glycerol ester polymer.

15. The composition of claim 1, further comprising a hydrophobic polymer, wherein the glycerol ester polymer serves as a solvent to the hydrophobic polymer.

16. The composition of claim 1, further comprising microparticles disposed within the glycerol ester polymer.

17. The composition of claim 1, wherein the backbone of the glycerol ester polymer is fully esterified and the active agent is hydrophobic.

18. The composition of claim 1, wherein the glycerol ester polymer has a viscosity of between 1,000 and 30,000 cP (centipoise) at 37 degrees Celsius.

* * * * *